(12) United States Patent
Troiano et al.

(10) Patent No.: US 7,943,668 B2
(45) Date of Patent: May 17, 2011

(54) PROCESS FOR PREPARING A PHARMACEUTICAL COMPOSITION WITH ANTI-INFLAMMATORY AND ANALGESIC ACTIVITY FOR ADMINISTRATION VIA A PATCH FOR EXTERNAL USE, AND COMPOSITION THUS OBTAINED

(75) Inventors: Angelo Troiano, Caslano (CH); Giorgio Zoppetti, Milan (IT)

(73) Assignee: Altergon S.A., Lugano (CH)

( * ) Notice: Subject to any disclaimer, the term of this patent is extended or adjusted under 35 U.S.C. 154(b) by 86 days.

(21) Appl. No.: 12/074,504

(22) Filed: Mar. 3, 2008

(65) Prior Publication Data

US 2009/0221707 A1 Sep. 3, 2009

(51) Int. Cl.
*A61P 29/00* (2006.01)
*A61P 25/04* (2006.01)
*A61K 31/196* (2006.01)

(52) U.S. Cl. ...................................... 514/567
(58) Field of Classification Search .................. None
See application file for complete search history.

(56) References Cited

U.S. PATENT DOCUMENTS 4,917,886 A * 4/1990 Asche et al. ................... 514/567

FOREIGN PATENT DOCUMENTS

| EP | 0271709 | * 11/1987 |
| EP | 0 621 263 A2 | 10/1994 |
| EP | 1 046 395 A1 | 10/2000 |

OTHER PUBLICATIONS

CR Tonussi (abstract only), Mechanism of diclofenac analgesia: direct blockade of inflammatory sensitization. Eur J Pharmacol 251: 173-179 (1994).*
A Arellano, Influence of propylene glycol and isopropyl myristate on the in vitro percutaneous penetration of diclofenac sodium from carbopol gels. Eur J Pharmaceut Sci 7: 129-135 (1998).*
Voltarol Gel Patch label and label history (http://emc.medicines.org.uk/document.aspx?documentId=16903) (2005 with 2007 update), accessed Sep. 2, 2009.*
Flector Patch label (http://www.accessdata.fda.gov/drugsatfda_docs/label/2007/021234lbl.pdf) (2005), accessed Sep. 1, 2009.*
Minghetti et al., "Ex Vivo Study of Transdermal Permeation of Four Diclofenac Salts from Different Vehicles," Journal of Pharmaceutical Sciences, vol. 96, No. 4, Apr. 2007.

* cited by examiner

*Primary Examiner* — Jeffrey S Lundgren
*Assistant Examiner* — Sara E Townsley
(74) *Attorney, Agent, or Firm* — Abelman, Frayne & Schwab

(57) ABSTRACT

The present invention relates to a process for preparing a pharmaceutical composition with anti-inflammatory and analgesic activity for administration via a patch for external use, its components including as active principle a salt of diclofenac, 2[(2,6-dichlorophenyl)amino]benzene-acetic acid, with a cyclic organic base chosen from hydroxyethylpyrrolidine or hydroxyethylpiperidine characterized in that said active principle is added to a mixture of one or more of said components, in the form of a solution in water and propylene glycol in a ratio of about 1:1 parts by weight.

4 Claims, No Drawings

PROCESS FOR PREPARING A PHARMACEUTICAL COMPOSITION WITH ANTI-INFLAMMATORY AND ANALGESIC ACTIVITY FOR ADMINISTRATION VIA A PATCH FOR EXTERNAL USE, AND COMPOSITION THUS OBTAINED

The present invention relates to a process for preparing a pharmaceutical composition with anti-inflammatory and analgesic activity for administration via a patch for external use.

EP0621263, in the joint name of Teikoku and the present applicant Altergon, describes a formulation suitable for administration in the form of an anti-inflammatory and analgesic patch for external transdermal use, based on a salt of diclofenac, i.e. 2[(2,6-dichlorophenyl)amino]benzene-acetic acid with a cyclic organic base, having the general formula

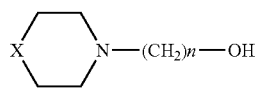

in which X is a group of formula —$(CH_2)$m- where m is the integer 0 or 1, and n is 2, and also comprising a pH adjuster and pharmaceutically acceptable components such as thickeners, humectants, preservatives and a cross-linking agent.

The diclofenac salt with the hydroxyethylpyrrolidine base is identified hereinafter by the abbreviation DHEP, while the salt with hydroxyethylpiperidine is identified by the abbreviation DHEPP.

The Teikoku/Altergon patent demonstrates experimentally that the patch in question shows high activity both in terms of increased transdermal permeation of the active principle and improved inhibition of oedema.

EP0621263 also describes a preparative process for said formulation, characterized by adding, always in an aqueous solution, the entire quantity of DHEP salt to the mixture of components as inferred from the descriptive examples of said patent.

In this respect, DHEP is characterized by a high solubility in water, up to about 40%, being 20 times greater than that of diclofenac sodium salt.

Regarding the remainder of the pharmaceutically acceptable components, EP0621263 involves the use, among others, of a compound selected from glycerol, propylene glycol, polyethylene glycol, 1,2-butanediol and a D-sorbitol solution as humectants in the final preparation.

The only example in EP0621263 that concerns the use of propylene glycol as a humectant is example 3, in which 10 parts % wt/wt of propylene glycol are added to the mixture after the entire quantity of DHEP, i.e. 0.65% wt/wt dissolved in water was already added to the mixture, in line with the aforestated general criteria.

An object of the present invention is to provide a process for preparing the formulation in EP0621263 which proves particularly advantageous from the industrial production viewpoint, where high quantities of mixture components are involved for which a stability of the solution over time is required. In this respect, although a low-volume solution can be quickly processed, at the industrial production stage the treatment of larger volumes requires long solubilization times, and therefore waiting time, prior to final production.

A further object of the present invention is to avoid for example component precipitation phenomena, particularly of the active principle, which would result in its incomplete solubilization, and consequent dishomogeneity of the final product, to hence ensure a sufficient time stability of the solution to be processed, independently of the quantities involved.

In accordance with the present invention, it has now been surprisingly found that these objects are advantageously attained by a process for preparing a pharmaceutical composition with anti-inflammatory and analgesic activity for administration via a patch for external use, its components including as active principle a salt of diclofenac, 2[(2,6-dichlorophenyl)amino]benzene-acetic acid, with a cyclic organic base chosen from hydroxyethylpyrrolidine or hydroxyethylpiperidine characterized in that said active principle is added to a mixture of one or more of said components, in the form of a solution in two solvents, namely water and propylene glycol, in a ratio of about 1:1 parts by weight.

The characteristics and advantages of the process of the present invention will be illustrated in greater detail in the following description.

The following examples of the present invention are given by way of non-limiting illustration.

Comparative example 1 is given for comparison purposes as an example of the prior art, in accordance with the process described in example 1 of the aforementioned EP0621263.

Comparative example 2 is given for comparison purposes as a further example of the prior art, in accordance with the process described in example 3 of the aforementioned EP0621263.

Example 1 relates instead to the process of the present invention.

COMPARATIVE EXAMPLE 1

14 kg of gelatin and 14 kg of polyvinylpyrrolidone are added to 210 kg of purified water and dissolved by heating to 60° C.

140 kg of D-sorbitol solution, 35 kg of kaolin, 3.5 kg of titanium dioxide, 0.7 kg of methylparaben, 0.35 kg of propylparaben and 2.1 kg of tartaric acid are added to the resulting solution, and the mixture is sufficiently mixed.

A dispersion composed of 28 kg of sodium polyacrylate, 21 kg of sodium CMC and 5.6 kg of aluminium hydroxide, dispersed in 140 kg of 1,3-butylene glycol, are added. The dispersion is added in several portions, with mixing after each addition.

Finally a solution of 9.1 kg of DHEP, dissolved in the remaining 76.65 kg of purified water, is added and the mixture is mixed until it becomes homogeneous.

The mixture thus obtained is spread over a non-woven fabric at 1000 g/m².

A plastic film is placed over the coated fabric and the combination is cut into pieces of the required size to obtain a patch as described in EP0621263. The final preparation has a pH of 7.9.

COMPARATIVE EXAMPLE 2

14 kg of gelatin and 21 kg of polyvinyl alcohol are added to 210 kg of purified water and dissolved by heating to 60° C.

210 kg of D-sorbitol solution, 35 kg of kaolin and 0.7 kg of propylparaben are added to the resulting solution, and the mixture is sufficiently mixed.

A solution of 4.55 kg of DHEP, dissolved in the remaining 80.85 kg of purified water, is then added and further mixing is carried out.

Finally a dispersion composed of 28 kg of sodium polyacrylate, 17.5 kg of sodium CMC and 8.4 kg of aluminium acetate dispersed in 70 kg propylene glycol are added and the mixture is mixed until it becomes homogeneous.

The mixture thus obtained is spread over a non-woven fabric at 1000 g/m$^2$.

A plastic film is placed over the coated fabric and the combination is cut into pieces of the required size to obtain a patch as described in EP0621263. The final preparation has a pH of 8.5.

EXAMPLE 1

Solutions or dispersions are prepared as described in the following steps:

Step A: 14 kg of gelatin and 14 kg of polyvinylpyrrolidone are added to about 112 kg of purified water, dissolved by heating to 50-65° C.

Step B: 21 kg of kaolin are dispersed in 120 kg of D-sorbitol solution.

Step C: 3.5 kg of titanium dioxide are dispersed in 10 kg of purified water.

Step D: 0.86 kg of EDTA are dissolved in 5 kg of purified water, heating to promote dissolution if necessary.

Step E: 0.7 kg of methylparaben and 0.35 kg of propylparaben are dissolved in 10.5 kg of propylene glycol.

Step F: 3.5 kg of tartaric acid are dissolved in 5 kg of water.

Step G: 21 kg of sodium CMC, 28 kg of sodium polyacrylate and 2.1 kg of aluminium glycinate are dispersed in 70 kg of butylene glycol.

Step H: 10 5 kg of propylene glycol are added to 10.5 kg of water and 9.1 kg of DHEP are dissolved in the mixture thus obtained, heating to 30-50° C.

The solutions/dispersions obtained in the aforesaid steps are poured into the mixer in the order described in the following sequence:
product of Step A
160 kg of D-sorbitol solution
product of Step B
40 kg of purified water
product of Step C
product of Step D, rinsing the container with 15 kg of purified water
product of Step E after adding 1.4 kg of polysorbate 80
0.14 kg of fragrance
product of Step F
the mixer is started, said product of Step G is added and mixed for 2 minutes
add said product of Step H, rinsing the container with about 10.25 kg of purified water then mix for a further 5 minutes 30 seconds in total until the mixture is homogeneous.

The mixture thus obtained is spread over a non-woven fabric at 1000 g/m$^2$. A protective plastic film is applied to the coated fabric and the combination is cut into pieces of the required size to obtain the patch of the invention.

By comparing the three aforegiven examples, it can be seen that in the prior art all the DHEP employed is added to the mixture of the required composition in the form of a solution in water alone, while in the case of the invention process, all the DHEP employed is added to the mixture of the required composition in the form of a solution in water and propylene glycol in a ratio of about 1:1 parts by weight, as described in example 1, step H.

Comparative example 2 shows that in the prior art propylene glycol is not used as a co-solvent with water for DHEP, but rather for obtaining a dispersion composed of sodium polyacrylate, sodium CMC and aluminium acetate, with the function of humectant in the final composition.

By experimentation it was found that the process of the present invention enables to avoid precipitation phenomena, which would otherwise lead to incomplete solubilization of the mixture, thus ensuring a sufficient time stability of the solution to be processed, independently of the quantities involved.

Since the process is hence suitable for handling large amounts of mixture based on the industrial scale preparation requirements of the composition in question, the objectives of the present invention are thus achieved.

The invention claimed is:

1. A process for preparing a pharmaceutical composition with anti-inflammatory and analgesic activity for administration via a patch for external use, comprising a hydroxyethylpyrrolidine or hydroxyethylpiperidine salt of diclofenac, comprising the step of adding the salt of diclofenac to a solution comprising water and propylene glycol, which are present in a ratio of about 1:1 parts by weight.

2. Process according to claim 1, comprising the following steps:
Step A: gelatin and polyvinylpyrrolidone are added to purified water, dissolved by heating to 50-65° C;
Step B: kaolin is dispersed in a D-sorbitol solution;
Step C: titanium dioxide is dispersed in purified water;
Step D: EDTA is dissolved in purified water;
Step E: methylparaben and propylparaben are dissolved in propylene glycol;
Step F: tartaric acid is dissolved in water;
Step G: CMC sodium, sodium polyacrylate and aluminium glycinate are dispersed in butylene glycol; and
Step H: propylene glycol is added to water in a ratio of about 1:1 parts by weight and the entire quantity of diclofenac salt with hydroxyethylpyrrolidine or hydroxyethylpiperidine is dissolved in the mixture thus obtained, heating to 30-50° C.

3. Process according to claim 2, comprising mixing the products of steps A through H in the following order:
product of Step A
D-sorbitol in solution
product of Step B
purified water
product of Step C
product of Step D
product of Step E to which polysorbate 80 has been added
product of Step F
add product of Step G
add product of Step H and mix until the mixture is homogeneous, thus giving rise to said composition.

4. Process according to claim 3, comprising mixing the products of steps A through H in the following order:
product of Step A
D-sorbitol in solution
product of Step B
purified water
product of Step C
product of Step D
purified water
product of Step E, to which polysorbate 80 has been added
fragrance
product of Step F
add product of Step G
add product of Step H
add purified water and mixing until the mixture is homogeneous, thus giving rise to said composition.

* * * * *